US008029282B2

(12) United States Patent
Carter

(10) Patent No.: US 8,029,282 B2
(45) Date of Patent: Oct. 4, 2011

(54) CARRY AND DRIVE DEVICE AND METHOD FOR DENTAL IMPLANT AND/OR COMPONENTS THEREOF

(75) Inventor: Robert D. Carter, Apple Valley, MN (US)

(73) Assignee: Keystone Dental, Inc., Burlington, MA (US)

( * ) Notice: Subject to any disclaimer, the term of this patent is extended or adjusted under 35 U.S.C. 154(b) by 98 days.

(21) Appl. No.: 11/855,779

(22) Filed: Sep. 14, 2007

(65) Prior Publication Data

US 2008/0050698 A1    Feb. 28, 2008

Related U.S. Application Data

(63) Continuation of application No. 11/201,175, filed on Aug. 10, 2005, now abandoned.

(51) Int. Cl.
*A61C 3/00* (2006.01)
(52) U.S. Cl. .......................... 433/163; 433/141; 433/173
(58) Field of Classification Search .................. 433/141, 433/163, 172, 173; 81/436, 121.1, 124.3
See application file for complete search history.

(56) References Cited

U.S. PATENT DOCUMENTS

| | | | |
|---|---|---|---|
| 5,019,080 A | 5/1991 | Hemer | |
| 5,105,690 A | 4/1992 | Lazzara et al. | |
| 5,207,132 A | 5/1993 | Goss et al. | |
| 5,279,190 A | 1/1994 | Goss et al. | |
| 5,690,489 A | 11/1997 | Carchidi | |
| 5,692,904 A | 12/1997 | Beaty et al. | |
| 5,823,776 A | 10/1998 | Duerr et al. | |
| 5,947,733 A * | 9/1999 | Sutter et al. | 433/173 |
| 5,964,591 A | 10/1999 | Beaty et al. | |
| 6,016,727 A | 1/2000 | Morgan | |
| 6,099,311 A | 8/2000 | Wagner et al. | |
| 6,159,008 A | 12/2000 | Kumar | |
| 6,217,332 B1 | 4/2001 | Kumar | |
| 6,419,489 B1 | 7/2002 | Jorneus et al. | |
| 6,454,567 B1 | 9/2002 | Carchidi et al. | |
| 6,561,805 B2 | 5/2003 | Kumar | |
| 6,626,067 B1 * | 9/2003 | Iwinski et al. | 81/121.1 |
| 7,131,840 B2 | 11/2006 | Constantino | |
| 2002/0177105 A1 * | 11/2002 | Engman | 433/173 |
| 2003/0113690 A1 * | 6/2003 | Hollander et al. | 433/173 |
| 2004/0101807 A1 * | 5/2004 | Porter et al. | 433/173 |
| 2005/0287497 A1 | 12/2005 | Carter | |

FOREIGN PATENT DOCUMENTS

| | | |
|---|---|---|
| DE | 29816210 | 3/1999 |
| EP | 0985498 A | 12/2004 |
| EP | 1481646 A | 12/2004 |
| JP | H11-512324 | 10/1999 |
| JP | 2003-052720 | 2/2003 |
| WO | 9812982 A1 | 4/1998 |
| WO | 0226448 A2 | 4/2002 |

OTHER PUBLICATIONS

English translation of Office Action issued in Japanese Patent Application No. 2007-519300 dated Jul. 8, 2010.

* cited by examiner

*Primary Examiner* — Cris L Rodriguez
*Assistant Examiner* — Eric Rosen
(74) *Attorney, Agent, or Firm* — Fish & Richardson P.C.

(57) ABSTRACT

A carry and drive device and method for a dental implant or a dental implant component with a driving recess. The device includes a drive end with a configuration substantially matching the drive recess and with an interference surface frictionally engageable with a portion of the driving recess.

16 Claims, 9 Drawing Sheets

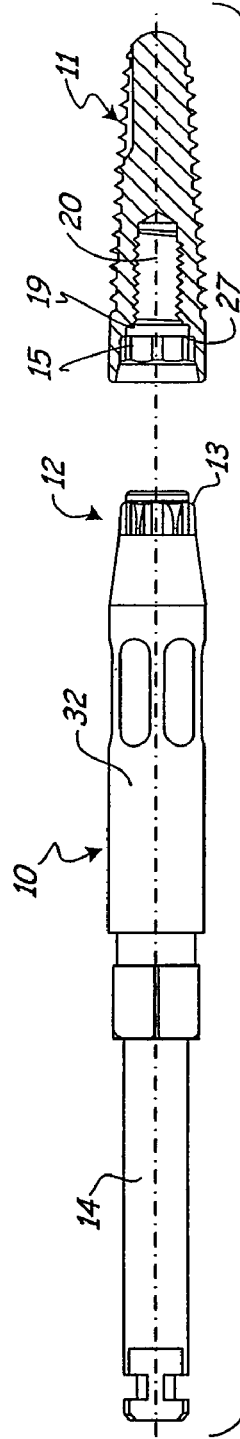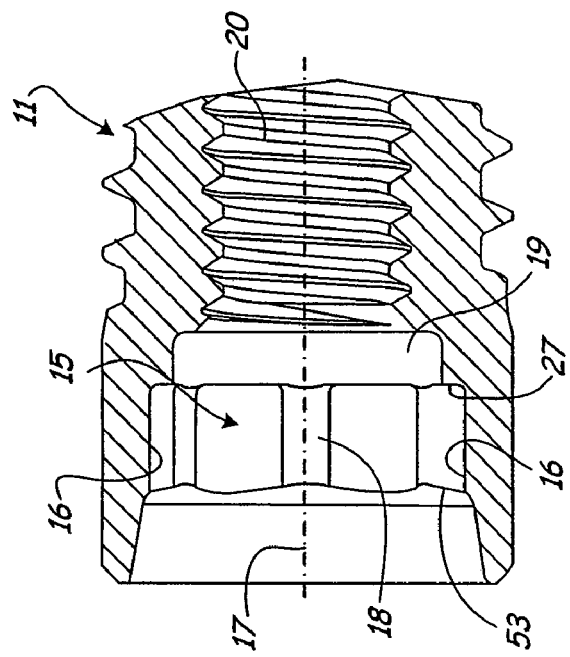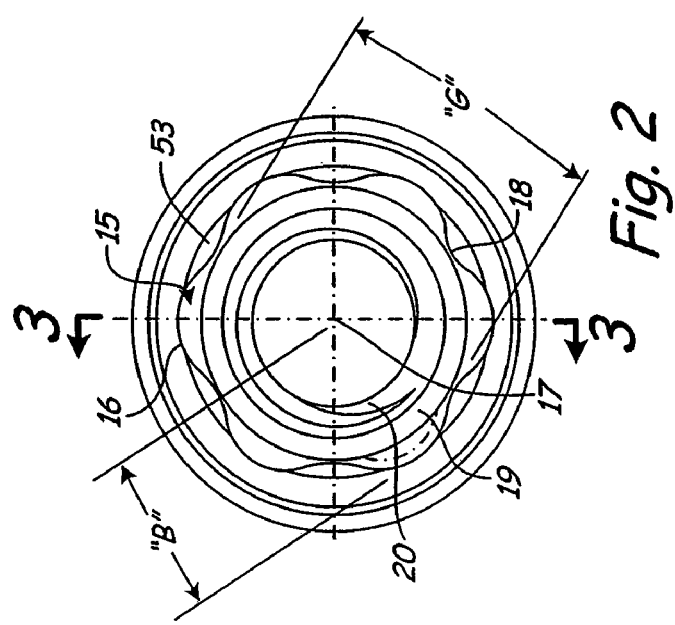

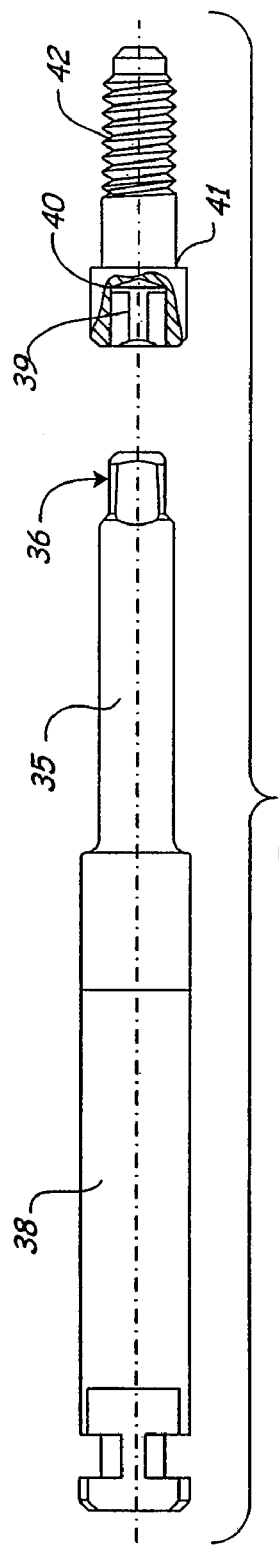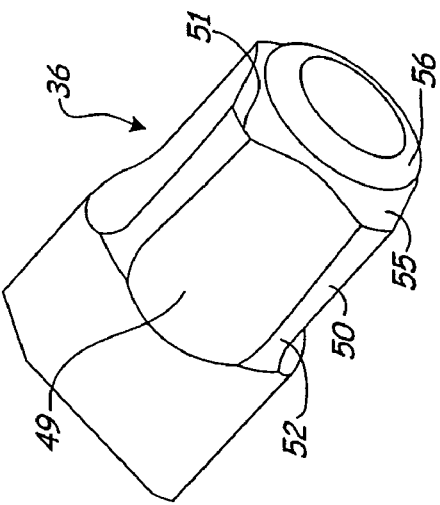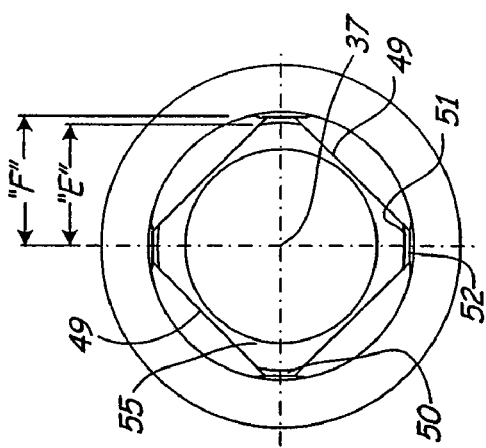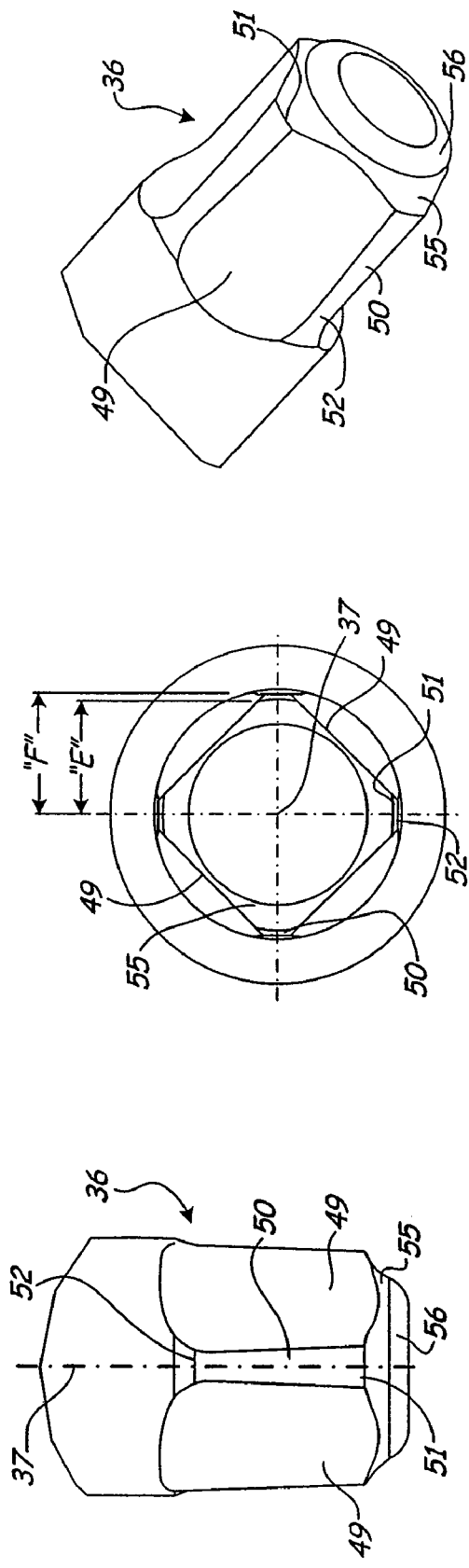
Fig. 8
Fig. 13
Fig. 12
Fig. 11

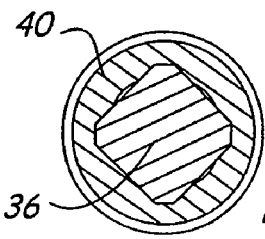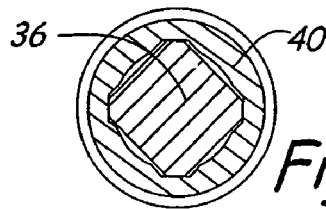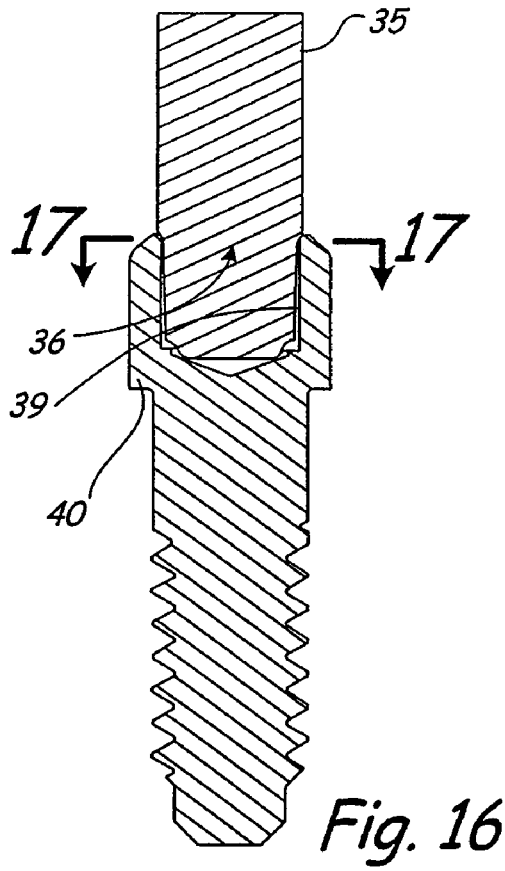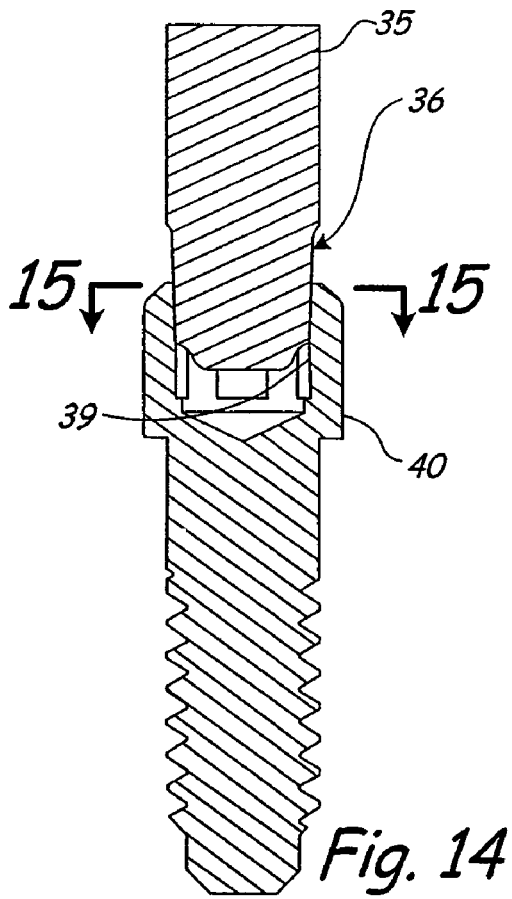

CARRY AND DRIVE DEVICE AND METHOD FOR DENTAL IMPLANT AND/OR COMPONENTS THEREOF

RELATED APPLICATIONS

This application is a continuation of U.S. application Ser. No. 11/201,175, filed on Aug. 10, 2005 now abandoned.

BACKGROUND OF THE INVENTION

1. Field of the Invention

The present invention relates generally to the field of dental implants and components thereof, and more specifically to a combination carry (or delivery) and drive device and method for a dental implant or components thereof. The invention also relates to the combination of a dental implant and a device and method for carrying and driving such implant and a combination of a dental implant abutment screw and a device and method for carrying and driving such screw.

2. Description of the Prior Art

A wide variety of dental implants currently exist in the art. Such dental implants commonly include a body with external threads or other means for mounting and retaining the implant within the patient's mouth. Installation of the implant commonly involves rotation of the implant into a predrilled or tapped site using a drive member such as a ratchet or other rotation means. The implant also includes a drive region which may be located externally or internally at or near the proximal end of the implant. Various structures for both externally and internally driving the implant currently exist. Certain types of dental implants also include abutment screws for connecting an abutment or the like to the implant. Various means also currently exist for accomplishing this installation.

During installation of the implant, it is desirable to deliver the implant to the predrilled or tapped site by transferring or carrying the implant from the sterile package or other environment to such site without breaching the sterile condition of the implant. Similarly, when installing an abutment with an abutment screw, it is desirable to deliver the abutment screw to the installation site without breaching its sterile condition. Although some mechanisms exist which are capable of both carrying the implant (or abutment screw) to the implant (or installation) site as well as driving the implant (or screw), there is a continuing need for an improved implant and/or abutment screw carrier and driver which overcomes limitations of prior art devices.

Accordingly, there is a need in the art for a carry and drive device and method by which a dental implant and/or for components thereof can be carried or delivered from a sterile environment to an installation site and then rotationally driven with a single device.

SUMMARY OF THE INVENTION

The present invention relates to a combination carry and drive device for carrying a threaded member to an installation site and for driving or rotating such threaded member into that site. The invention has particular applicability to the field of dental implants as a device for carrying an implant to an installation site and rotationally driving such implant into the installation site and/or carrying a dental implant component such as an abutment screw to an installation site and rotationally driving the screw into the implant to connect the abutment.

More specifically, the combination carry and drive device of the preferred embodiment of the present invention is designed for use with a rotation member such as a dental implant or an abutment screw which is provided with an internal driving recess having one or more driving surfaces or lobes. The carry and drive device includes a driver end which is designed for insertion into the driving recess and which has an exterior configuration substantially matching the driving configuration of the driving recess. In the preferred embodiment, the driver end also includes an interference or engagement surface designed for carrying engagement with a portion of the driving recess. This interference or engagement surface is preferably beveled inwardly toward its distal end so that the radial dimension of such surface at its distal end is less than the radial dimension of a corresponding portion of the driving recess and the radial dimension of such surface at its proximal end is greater than the radial dimension of a corresponding portion of the driving recess.

During use, the driver end of the device is inserted into the driving recess of the implant. After limited insertion, a portion of the interference surface engages a corresponding portion of the driving recess. Upon further insertion, a tight friction fit occurs between such interference surface and its corresponding driving recess portion. This friction fit is sufficient to carry the driven member to its desired installation site. When the installation site is reached, the driven member is installed by rotationally driving such member with the driver end.

In the preferred embodiment, the device for carrying and driving an implant includes an internal connection dental implant with a driving recess comprised of a plurality of concave and convex lobes defining the driving surfaces. The driver end for this embodiment includes an external surface with substantially matching lobes and driving surfaces for insertion into the driving recess. The external surface of one or more of the driver end lobes is provided with an interference rib or portion extending outwardly from the exterior surface thereof. A beveled interference surface is formed from such interference rib and a distal portion of the driver end lobe so that a distal or outer end of such interference surface has a radial dimension less than a corresponding portion of the driving recess and an opposite or proximal end of such surface has a radial dimension greater than a corresponding portion of the driving recess.

The method of making and/or using the implant carry/driver device of the preferred embodiment includes providing a carrier having a driving configuration substantially matching the driving configuration of the driving recess and an interference rib or portion on the external surface of the driver in which the radial dimension of the driver end at the interference rib is greater than the radial dimension of the corresponding portion of the driving recess. A portion of the interference rib is then removed to form the interference surface. The method of using the implant carry and driver device includes inserting the driver into the driving recess until the interference surface is sufficiently engaged with a corresponding lobe of the driver recess, carrying or delivering the engaged implant to the installation site and rotating the implant at the site with the driver.

The carry and drive device for the abutment screw in accordance with the preferred embodiment is designed to carry and drive an abutment screw having a driving recess and a driving configuration comprised of a substantially square cross-section. The exterior configuration of the driver end of the carry and drive device for such abutment screw substantially matches the driving configuration of the abutment screw, but with one or more interference surfaces formed at its corners. Such interference surface inclines or is beveled inwardly toward its distal end. As with the implant carry and drive device, the interference surface of the carry and drive device for the abutment screw has a radial dimension at its distal end which is less than the radial dimension of a corresponding corner portion of the driving recess in the abutment screw and a radial dimension at its proximal end which is greater than the radial dimension of a corresponding corner portion of the driving recess in the abutment screw.

During use, the distal end of the carry and drive device is inserted into the driving recess of the abutment screw until there is engagement between the interference surface and a corresponding corner portion of the driving recess. Upon further insertion, sufficient frictional engagement is provided between such interference surface and the corresponding portion of the driving recess to carry the abutment screw to its installation site. Upon reaching the installation site, the abutment screw is positioned within the abutment and rotated by the driver end.

Accordingly, the carry and drive device in accordance with the preferred embodiment of the present invention is designed for use with a dental implant or a dental implant component such as an abutment screw which includes a driving recess with one or more drive surfaces. The driver end of the device includes a configuration substantially matching the driving recess and one or more driving surfaces for driving engagement with the driving surfaces of the recess upon insertion of such driver end. Either an interior surface portion of the recess or an exterior surface portion of the driver end is provided with an interference surface. Preferably, at least a portion of the interference surface is positioned radially inwardly of the interior surface of the recess (or radially outwardly of the exterior surface of the driver) so that upon insertion of the driver end into the driving recess, frictional engagement or interference will result. This enables the driver end and the implant (or abutment screw) to be frictionally engaged to permit the implant or abutment screw to be carried to the installation site and then rotated.

Further, details regarding the invention are described with reference to the drawings, the description of the preferred embodiment and method and the appended claims.

DESCRIPTION OF THE DRAWINGS

FIG. 1 is a side elevational view of the implant carry and drive device and the dental implant with which it is used.

FIG. 2 is an elevational view of the dental implant as viewed from its proximal end.

FIG. 3 is an enlarged, fragmentary view, partially in section, of the proximal end portion of the dental implant as viewed along the section line 3-3 of FIG. 2.

FIG. 8 is an elevational side view of the abutment screw carry and drive device and an abutment screw with which it is used.

FIG. 11 is an enlarged, fragmentary elevational side view of the distal end of the abutment screw carry and drive device of FIG. 8.

FIG. 12 is an elevational view of the abutment screw and carry drive device of FIG. 8 as viewed from the distal end.

FIG. 13 is an isometric, fragmentary view of the distal end portion of the abutment screw and drive device of FIG. 8.

FIG. 14 is a view, partially in section, showing partial insertion of the abutment screw carry and drive device into the driving recess of the abutment screw.

FIG. 15 is a view, partially in section, as viewed along the section line 15-15 of FIG. 14.

FIG. 16 is a view, partially in section, showing the abutment screw carry and drive device fully inserted into the driving recess of the abutment screw.

FIG. 17 is a view, partially in section, as viewed along the section line 17-17 of FIG. 16.

DESCRIPTION OF THE PREFERRED EMBODIMENT AND METHOD

Figure 4:
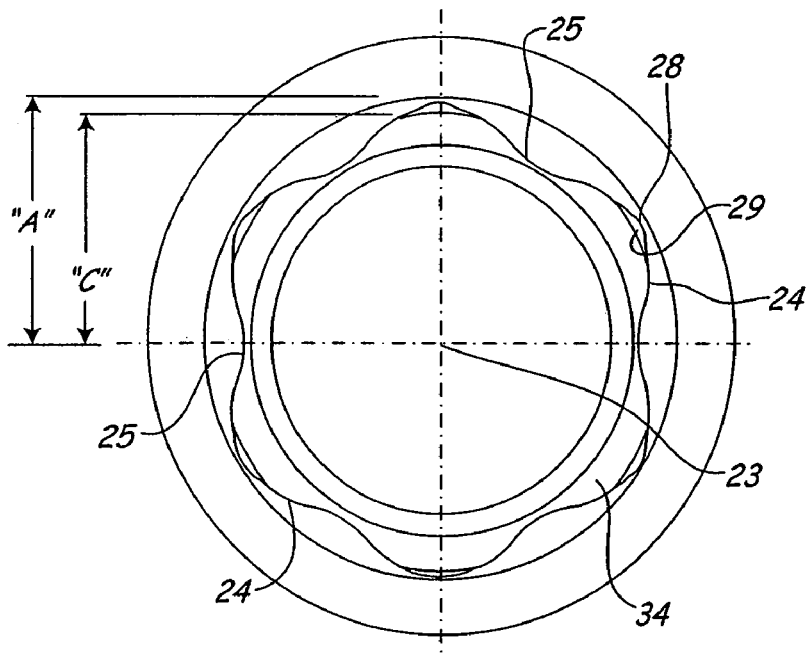
FIG. 4 is an elevational view of the implant driver of FIG. 1 as viewed from the distal end.
Figure 5:
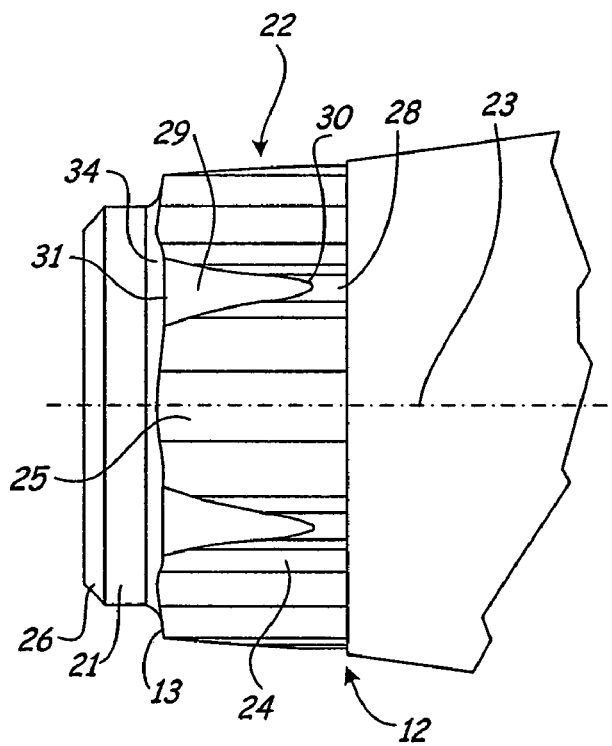
FIG. 5 is an enlarged, fragmentary side elevational view of the distal, driver end of the implant carry and drive device of FIG. 1.
Figure 6:
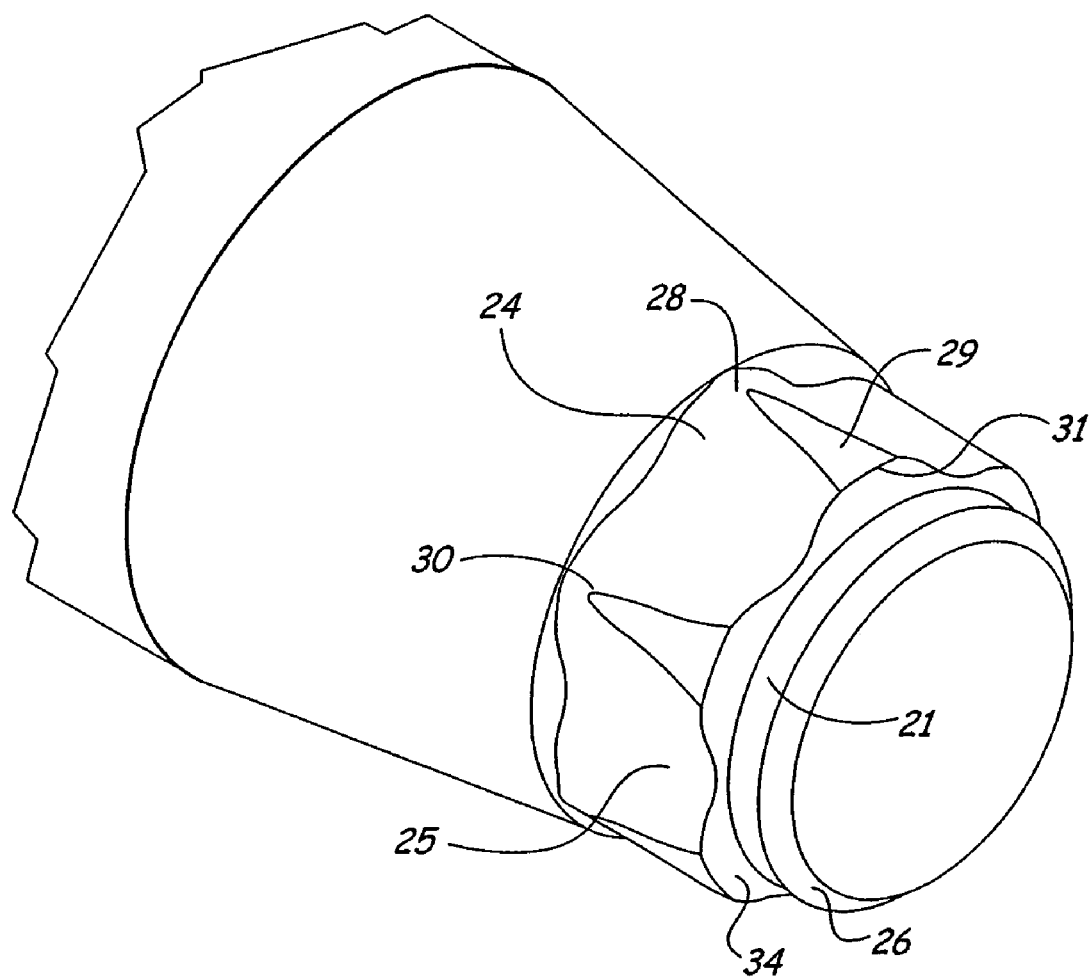
FIG. 6 is an isometric, fragmentary view of the distal end portion of the implant carry and drive device of FIG. 1.
Figure 7:
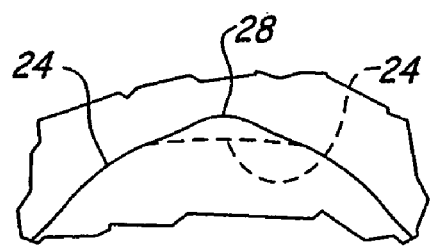
FIG. 7 is an enlarged, fragmentary sectional view of one of the lobes of the driver showing the interference rib relative to the lobe configuration prior to formation of the interference surface.

The present invention is directed to a carry and drive device for a rotation member. Although the rotation member normally includes external threads and can take a variety of forms, the invention has particular applicability to a carry and drive device for a dental implant and/or various components of a dental implant assembly such as an abutment screw. Accordingly, the preferred embodiment and method will be described with respect to a carry and drive device for use with a dental implant (FIGS. 1-7) and a carry and drive device for use with an abutment screw for a dental implant (FIGS. 8-17).

Throughout the application, the terms "proximal" and "distal" will be used in defining various components, surfaces, shoulders, ends, etc. of the device and other structures of the present invention. Unless otherwise indicated "proximal" for the carry and drive device shall mean the component, surface, shoulder, end, etc. furthest from the driver end of such device or, for the rotation member, shall mean the component, surface, shoulder, end, etc. furthest from the threaded end of the rotation member, while "distal" for the carry and drive device, shall mean the component, surface, shoulder, end, etc. closest to the driver end of such device or, for the rotation member, shall mean the component, surface, shoulder, end, etc. closest to the threaded end of the rotation member.

With general reference to FIGS. 1-7 and more specific reference to FIG. 1, the implant carry and drive device 10 is shown together with a dental implant 11 with which it is designed for use. In general, the device 10 is an elongated device which includes a driver end 12, a shank portion 14 for connection to a dental hand piece or other rotation device and an intermediate shank or rotation shaft 32 between the driver end 12 and the shank 14. The driver end 12 is designed for insertion into a driving recess 15 near the proximal end of the implant 11. As will be described below, insertion of the end 12 into the recess 15 results in frictional engagement between portions of the end 12 and the recess 15 to permit the implant 11 to be carried from a sterile package or other environment to the installation site and, when so delivered, to install the implant by rotation.

With continuing reference to FIG. 1 and also reference to FIGS. 2 and 3, the implant 11 is what is referred to as an internal connection implant. The proximal end of the implant 11 includes an internal driving recess 15 defined by a plurality of drive surfaces comprised of concave and convex driving lobes 16 and 18. A pilot recess 19 is positioned below or on the distal side of the recess 15 and the lobes 16 and 18. A threaded recess 20 to receive an abutment screw is positioned below or on the distal side of the pilot recess 19. A beveled or lead-in surface 53 is provided at the proximal end of each of the convex lobes 18, between, the concave lobes 16, to assist in aligning the driver end 12 relative to the recess 15 as will be described in greater detail below. The implant 11 is generally elongated and includes a longitudinal axis 17. In the preferred embodiment, the lobes 16 and 18 are straight walled lobes in that they are defined by walls which are substantially parallel to one another and to the longitudinal axis 17. Further details regarding the structure of the implant 11 and the driving recess 15 are shown and described in copending U.S. patent application Ser. No. 10/879,824 filed Jun. 29, 2004, the entirety of which is incorporated herein by reference.

Reference is next made to FIGS. 4-7 showing details of the driver end 12 of the carry and drive device 10. The driver end 12 includes a driver portion 22, a distal pilot end portion 21 and a longitudinal axis 23. The driver portion 22 includes an exterior configuration substantially matching the interior surface configuration of the driving recess 15. As shown, this exterior configuration of the driver portion 22 includes a plurality of convex and concave driver lobes 24,25 which substantially conform to or match the concave and convex lobes 16 and 18 of the interior surface of the driving recess 15. Except for the presence of the interference rib or ribs 28 as will be discussed in greater detail below, the exterior dimensions of the lobed configuration of the driver portion 22 are slightly less than the interior dimensions of the recess 15 to permit the portion 22 to be inserted fully within the driving recess 15 and to drive or rotate the implant 11 after such insertion. Except for the interference rib or ribs 28 discussed below, the walls of the lobes 24 and 25 are straight walled lobes which are generally parallel to one another and to the longitudinal axis 23. A beveled or lead-in surface 34 is provided at the distal end of the driver portion 22 to assist in aligning the driver end 12 relative to the recess 15 as will be discussed in greater detail below.

The pilot end 21 is a short, generally cylindrical portion which is positioned at the distal end of the driver end 12 and is designed for insertion into the pilot bore 19 of the implant 11. This insertion ensures proper seating of the lobes 24 and 25 relative to the lobes 16 and 18 and provides stability between the driver end 12 and the implant 11 during rotational installation of the implant 11. A lead-in or beveled surface 26 is provided at the distal end of the pilot end 21 to assist in locating and positioning the driver end 12 within the recess 15 and within the pilot bore 19.

To provide the driver end 12 with its implant carrying ability, an interference means or mechanism in the form of the interference rib or portion 28 and the interference surface 29 is formed on each of the convex lobes 24 of the portion 22. As shown best in FIGS. 6 and 7, the interference rib or portion 28 comprises a rib or portion which extends outwardly from the outermost portion of the convex lobes 24 so that the radial dimension "A" (FIG. 4) at the outermost point of the ribs 28 is greater than the radial dimension "B" (FIG. 2) defining the outermost ends of the concave lobes 16 of the recess 15. As used herein with respect to the ribs 28, the surface 29, the lobes 16 or the ribs, interference surfaces, lobes, etc. of the abutment screw device described below, the "radial dimension" shall mean the radial distance between such rib, surface, lobe, etc. and its corresponding longitudinal axis.

The interference surface 29 on each of the lobes 24 is defined by a beveled surface which extends from a point 30 (the proximal end of the surface 29) on the interference rib 28 to the distal end 31 of the surface 29. As shown, this interference surface 29 is beveled or slopes inwardly from its proximal end 30 toward its distal end 31 so that the radial dimension "C" (FIG. 4) of the surface 29 at its distal end 31 is less than the radial dimension "B" of the corresponding concave lobe 16 (FIG. 2). In the preferred embodiment, the surfaces 29 are substantially flat, planar surfaces, although they can, if desired, be surfaces which have a slight curve. Such slight curve can be either a slight axial curve (either concave or convex) or a slight radial curve (either concave or convex).

With this structure, insertion of the driver end 12 into the driving recess 15 of the implant 11 will, at some point, result in interference or frictional engagement between a portion of the interference surface 29 and a proximal end or engagement surface portion of the concave lobes 16. Upon further insertion of the end 12 into the recess 15, some limited deformation and a tight frictional fit will occur between the concave lobes 16 and the interference surface 29. This frictional engagement between the driver end 12 and the driving recess 15 enables the implant 11 to be carried by the driver 10 to the installation site without any external tools or other means engaging the sterile implant.

The extent to which the end 12 can be inserted into the driving recess 15 beyond the initial contact point between the interference surface 29 and the proximal end of the concave lobes 16 is dependent upon various factors including, the materials from which the implant 11 and the driver 12 are constructed, the radial dimension "A" of the interference rib 28, the radial dimension "C" of the distal end 31 and the point along the surface 29 at which initial contact with the lobe 16 is made. In the preferred embodiment, it is desirable for the end 12 to be inserted into the recess 15 as far as possible without the distal ends of the lobes 24 and 25 "bottoming out". What this means is that insertion of the end 12 should stop, or be limited, prior to engagement between the distal end 13 of the driver end 22 (FIG. 5) and the distal end surface 27 (FIG. 3) of the recess 15. Insertion of the driver end 22 into the recess 15 should also preferably be a distance which is sufficient to allow the pilot 21 (FIG. 5) to be seated within the pilot bore 19 of the implant 11. This provides stability and proper alignment and engagement between the driving surfaces of the driver and implant lobes during rotation of the driver, and thus the implant. Preferably, initial engagement between the surface 29 and the distal ends of the lobes 16 should occur when the end 12 is inserted between about 20 and 80% and more preferably, between about 30 and 70%.

The carry and drive device 10 is manufactured by forming the driver end 12 with the interference ribs 28 extending the entire length of the lobes 24. Following this, the surfaces 29 are formed by removing a portion of the ribs 28 and a portion of the distal ends of the convex lobes 24 so that the radial dimension "C" (FIG. 4) is less than the radial dimension "B" (FIG. 2) and the initial point of engagement between the surface 29 and the distal ends of the lobes 16 upon insertion of the end 12 occurs at a point between the distal and proximal ends of the surface 29.

In the preferred embodiment, each of the convex lobes 24 is provided with an interference rib or portion 28 and a corresponding interference surface 29. However, it is contemplated by the present invention that such ribs and surfaces could be provided on less than all of the convex lobes 24. In general, however, providing interference ribs and corresponding interference surfaces on fewer of the lobes 24 will result in a lesser carrying force. However, benefits of the carrying feature of the present invention can still be achieved with a structure in which at least one of the convex lobes is provided with an interference rib 28 and a corresponding interference surface 29 provided the dimensional relationship between such surface and corresponding lobe is sufficient to provide the desired carrying force.

It is also contemplated that an interference rib and a corresponding interference surface could be formed on the concave lobes 25 of the lobed configuration 22. In a structure of this type, the interference surface would engage the convex lobes 18 of the recess 15 and result in a frictional fit between those elements. Such a structure would still provide sufficient carrying force between the device 10 and the implant 11.

It is also contemplated that one or more lobes of the implant 11, rather than the lobed portion 22 of the driver end 12, could be provided with an interference rib and a corresponding interference surface. In such a structure, the rib and surface of the implant lobes would frictionally engage corresponding portions of the driver lobes 24 and/or 25. Also, in such a structure, the radial dimensions of the proximal and distal ends of the interference surface would be compared to the radial dimension of the corresponding driver lobe. Specifically, in such an embodiment, the proximal end of the implant interference surface would be greater than the radial dimension of the corresponding driver lobe and the radial dimension of the distal end of the implant interference surface would be less than the radial dimension of the corresponding driver lobe.

Further, while the implant 11 is an internal connection implant with an internal driving recess, the invention is equally applicable to an externally driven implant in combination with a driver having an internal driving recess.

Accordingly, the invention can be characterized as a dental implant carry and drive assembly in which either the implant or the driver includes an inner driving recess having one or more drive surfaces or lobes and in which the other of the implant or the driver includes an exterior configuration substantially matching the configuration of the inner driving recess and having one or more corresponding driving surfaces or lobes. Further, at least a portion of the implant or driver is required to include interference means such as an interference surface, in which the respective radial dimensions of the interference surface and the corresponding lobe or drive surface with which it is engaged provide sufficient frictional engaging interference.

To use the device 10 of the present invention, the end 12 is inserted into the driving recess 15 of an implant 11. Preferably this is when the implant 11 is still at least partially in its package or in some other sterile condition. Such insertion is continued until sufficient frictional engagement is made between the surface 29 and the distal ends of the lobes 16 and until the pilot 21 is positioned within the pilot bore 19. The implant 11 is then carried by the device 10 to the installation site and the implant is rotated by the device 10 until it is installed to the desired position.

Reference is next made to FIGS. 8-16 showing details of the carry and drive device for use with a dental implant component such as an abutment screw. An abutment screw is used for connecting an abutment to the implant, such as the abutment shown in copending U.S. patent application Ser. No. 10/879,824, filed Jun. 30, 2004, the entirety of which is incorporated herein by reference. Although the carry and drive device shown in FIGS. 8-17 differs in many respects from the specific construction of the implant carry and drive device of FIGS. 1-7, there are various features of the abutment screw carry and drive device which are common with the implant carry and drive device. These include the driven element having a driving recess with one or more drive surfaces or lobes, a drive member having an exterior drive configuration substantially matching that of the driving recess and an interference surface formed on a portion of the exterior surface of the drive member. Further, the distal end of the interference surface has a radial dimension less than the radial dimension of a corresponding portion of the driving recess and the proximal end of such surface has a radial dimension greater than the radial dimension of a corresponding portion of the driving recess. The specific and preferred structure of the abutment screw carry and drive device is described as follows.

With reference to FIG. 8, the carry and drive device 35 for the abutment screw is generally elongated and includes a driver end 36 and a rearward shank portion 38 for connection to a dental hand piece or other rotation means. During use, the driver end 36 is inserted into a driving recess 39 of an abutment screw 40. The abutment screw 40 includes a shoulder portion 41 and a threaded portion 42 for securing an abutment (not shown) to a dental implant. As described below, insertion of the carry and drive end 36 into the recess 39 results in carrying engagement between the end 36 and the recess 39 so that the screw 40 can be removed from a package or other sterile environment and delivered to the installation site and, when there, be rotationally driven to secure the abutment to the implant.

Figure 9:
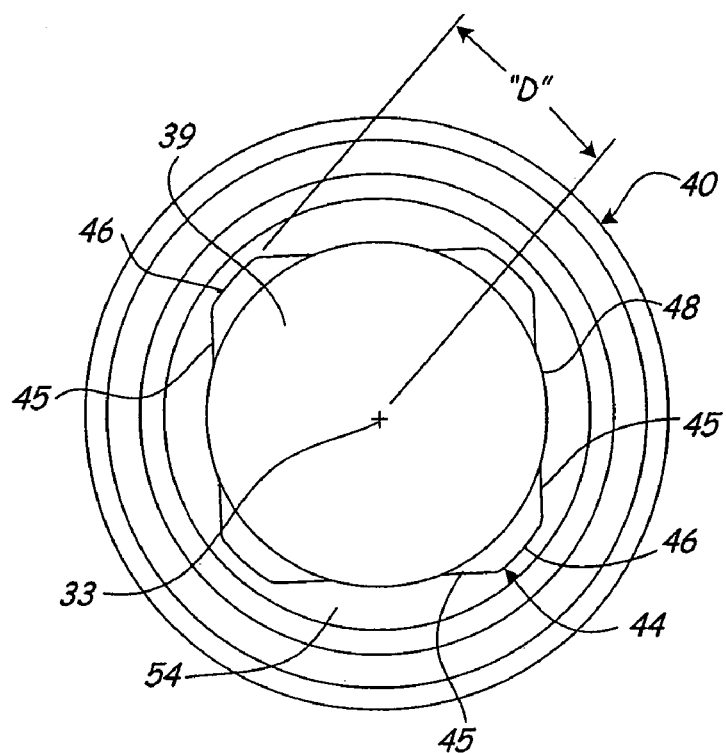
FIG. 9 is an elevational view of the abutment screw as viewed from its proximal end.
Figure 10:
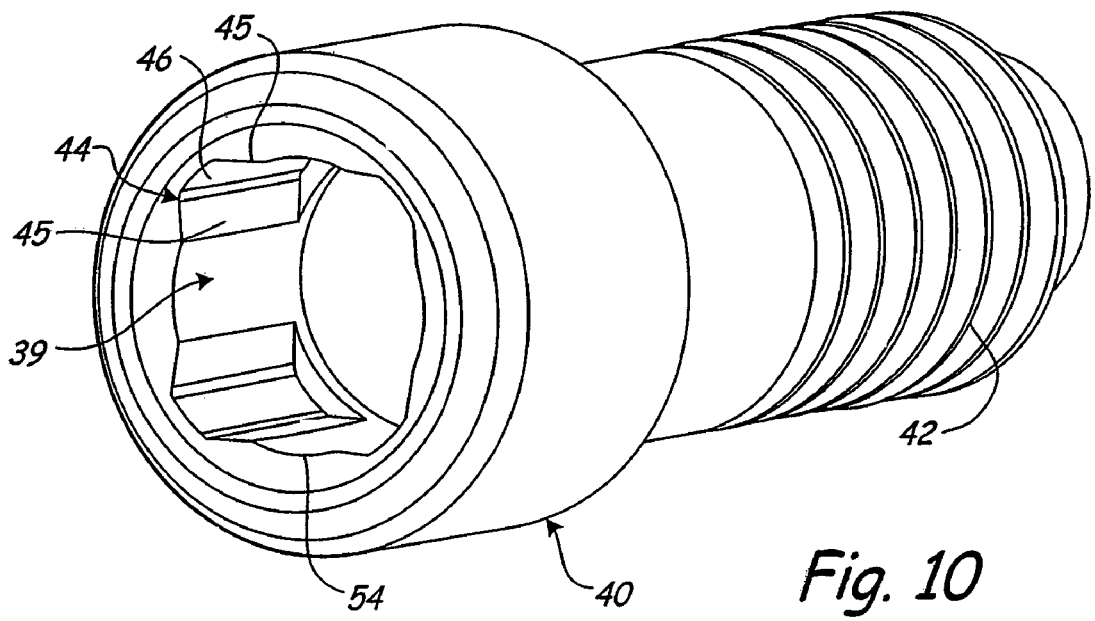
FIG. 10 is an isometric view of the abutment screw.

As shown best in FIGS. 9 and 10, the proximal end of the abutment screw 40 is provided with the driving recess 39. As shown, the recess 39 has a driving configuration which is roughly a square having four driving portions or driving lobes 44. Each of the driving portions or lobes 44 includes a driving surface or pair of driving surfaces 45 and a radial, end portion 46. In the preferred embodiment, the driving surface portions 45 comprise side surface portions of a substantially square configuration. Accordingly, the driving surfaces 45 on opposite sides of the end portions 46 are disposed relative to one another at approximately 90°. In the embodiment shown in FIGS. 9 and 10, the end portions 46 of the lobes or drive portions 44 have a radial dimension which is spaced a radial distance "D" (FIG. 9) from the longitudinal center axis 33 of the recess 39. Preferably, the drive surfaces 45, the end surfaces 46 and the other wall surfaces of the recess 39 are straight walled surfaces in which the surfaces are substantially parallel to one another and parallel to the axis 33. Lead-in or beveled surface portions 55 and 56 are provided at the distal end of the driver end 36 to assist in locating and positioning the end 36 within the recess 39.

In the preferred embodiment, the driving recess 39 in the screw 40 is formed by first boring a cylindrical hole 48 and then forming the lobes or drive portions 44 via a "broach" process. Accordingly, the broaching process is utilized to form the drive surfaces 45 as well as the end surfaces 46. As shown, the diameter of the cylindrical bore 48 is slightly larger than the lateral dimensions of the generally square configuration defined by the drive surfaces 45; however, this does not need to be the case. One reason for first forming the bore 48 by conventional means such as drilling or machining is to remove as much material as possible prior to the broaching process to form the drive lobes or portions 44.

Reference is next made to FIGS. 11, 12 and 13 showing various views of the driver end 36. The driver end 36 has a generally square cross-sectional configuration, with four generally planar side surfaces 49. In the preferred embodiment, these side surfaces 49 are drive surfaces which, when the end 36 is inserted into the recess 39, engage the drive surface portions 45 to rotate the screw 40. Accordingly, the lateral dimension between opposite side surfaces 49 is slightly less than the lateral dimension between opposite drive surfaces 45 to allow the end 36 to be inserted into the recess 39, but with a small enough tolerance so that, upon insertion, good driving engagement is made between the surfaces 49 and 45.

Positioned between each adjacent side surface 49 of the end 36 is an interference surface 50. In FIGS. 11 and 13, each interference surface 50 includes a distal end 51 and a proximal end 52, with the distal end 51 being located at or near the distal end of the surfaces 49 and the proximal end 52 being located at or near the proximal end of the surfaces 49.

In the preferred embodiment, the interference surfaces 50 are beveled and incline inwardly toward the axial center 37 of the end 36 as the surfaces 50 extend from the proximal end 52 to the distal end 51. In the preferred embodiment, these surfaces 50 are substantially planar surfaces, although they could also be slightly curved either radially (convex or concave) or axially (concave or convex). As shown best in FIG. 12, this results in a structure in which the radial dimension "E" of the surface 50 at the distal end 51 is less than the radial dimension "F" of the surface 50 at the proximal end 52. Further, the relationship between interference surfaces 50 and the end surfaces 46 of the recess 39 is such that the radial dimension "E" at the distal end 51 of the surface 50 is less than the radial dimension "D" (FIG. 9) of the end surface 46 and the radial dimension "F" of the surface 50 at the proximal end 52 is greater than the radial dimension "D" of the surface 46. Thus, at some location between the distal end 51 and proximal end 52 of the surface 50, the radial dimension of the surface 50 equals the radial dimension "D" of the end surfaces 46.

With this structure, as the end 36 is inserted into the driving recess 39, an insertion point will be reached at which the surfaces 50 will engage the proximal end of the surfaces 46. This will occur at a point where the radial dimension of the surface 50 equals the radial dimension "D" of the surface 46. Then, upon further insertion of the end 36, a tight frictional fit or engagement enables the abutment screw 40 to be carried from its sterile environment to its installation site and for the screw 40 to then be rotationally driven as a result of engagement between the drive surfaces 49 and the drive surfaces 45. During this further insertion, some limited deformation will occur between the surfaces 50 and the corresponding drive surfaces 45. Because the material from which the screw 40 is constructed (a titanium alloy) is softer than the material of the driver end 36, such limited deformation will occur in the drive surfaces 45. After installation of the screw 40 by rotation is complete, the driver end 36 is easily withdrawn from the recess 39.

FIGS. 14-17 show the manner of using the device 35 to carry and drive the abutment screw 40. Specifically, FIGS. 14 and 15 show the end 36 of the device 35 partially inserted into the recess 39 and to a point where the radial dimension of the surfaces 50 are substantially equal to the radial dimension "D" of the surfaces 46. Then, upon further insertion to the point shown in FIGS. 16 and 17, the surface 50 and the end surface 46 become frictionally engaged. This permits the screw 40 to be carried or delivered from its sterile package or other environment to its installation site and then installed by rotationally driving the screw 40 with the device 35.

In addition to the carry and drive feature of the device of the present invention, the carry and drive device of FIGS. 1-7 and the carry and drive device of FIGS. 8-17 also include a self-aligning feature which assists in quickly and easily causing the lobes or drive surfaces of the driver ends to be operationally aligned with their corresponding drive lobes in the implant 11 or the abutment screw 40. The means for accomplishing this includes lead-in or beveled surface portions at or near the distal ends of the carry and drive devices and their corresponding implant or screw surfaces and/or dimensional relationships between the driver ends and corresponding driving recesses.

Figure 19:
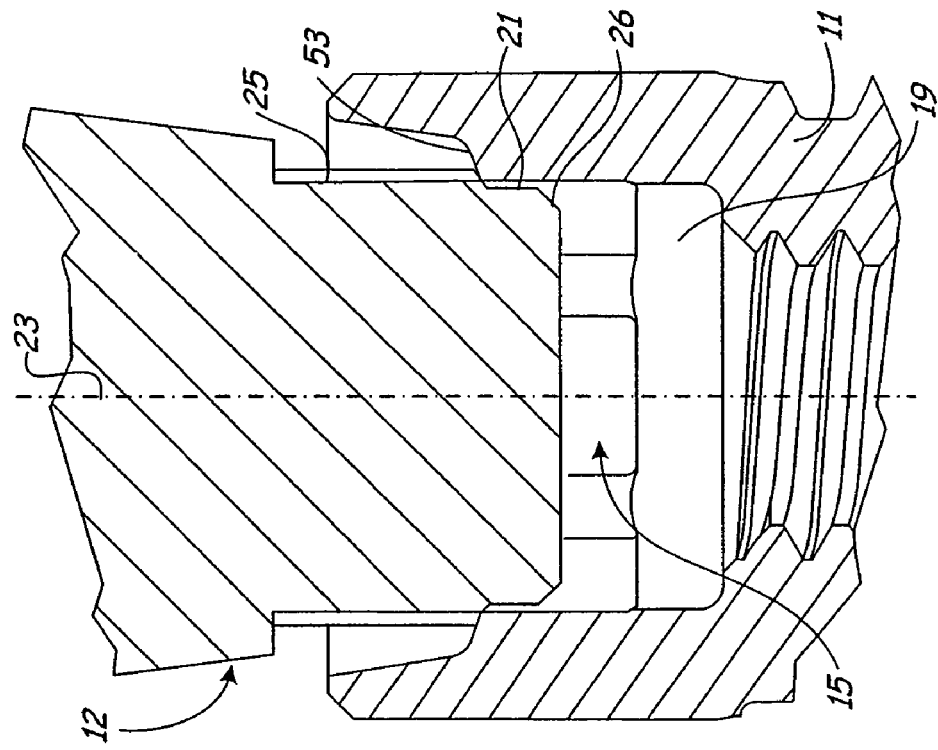
FIG. 19 is a sectional view, similar to FIG. 18, except with the driver end being aligned.
Figure 18:
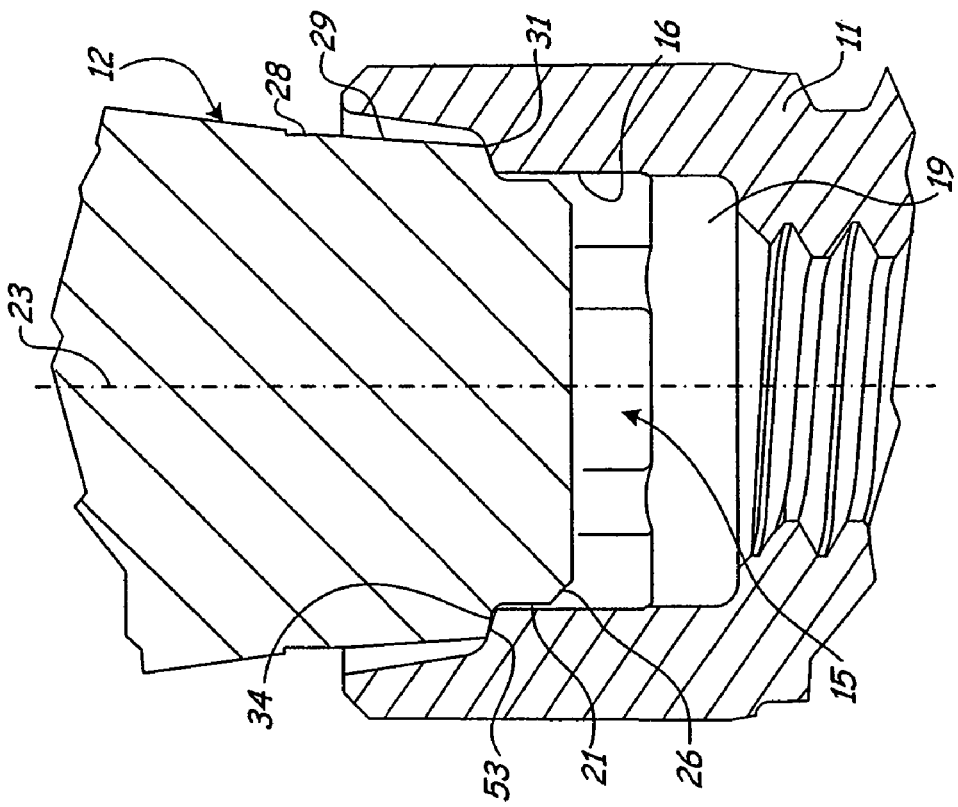
FIG. 18 is a sectional view showing partial insertion of a misaligned driver end into the implant driving recess.

Specifically, reference is made to FIGS. 18 and 19 showing cross sections of a misaligned driver end 12 (FIG. 18) and an aligned driver end 12 (FIG. 19). If the driver end 12 is inserted into the driving recess 15 of the implant 11 in a misaligned position as shown in FIG. 18, the driver end 12 will be axially aligned with the driving recess 15 because of the beveled surface 26 and the fact that the outer diameter of the pilot end 21 closely matches the diameter "G" (FIG. 2) defining the innermost surfaces of the convex lobes 18. Accordingly, when the end 12 is initially inserted into the recess 15, it is immediately axially aligned. Then, to the extent there is any misalignment between the lobes of the driver end 12 and the corresponding lobes of the recess 15, such lobes are quickly aligned upon rotation of the driver end 12. This alignment is assisted by engagement between the beveled or radiused surface 34 of the driver end 12 and the beveled or radiused surface 53 of the implant 11.

Figure 20:
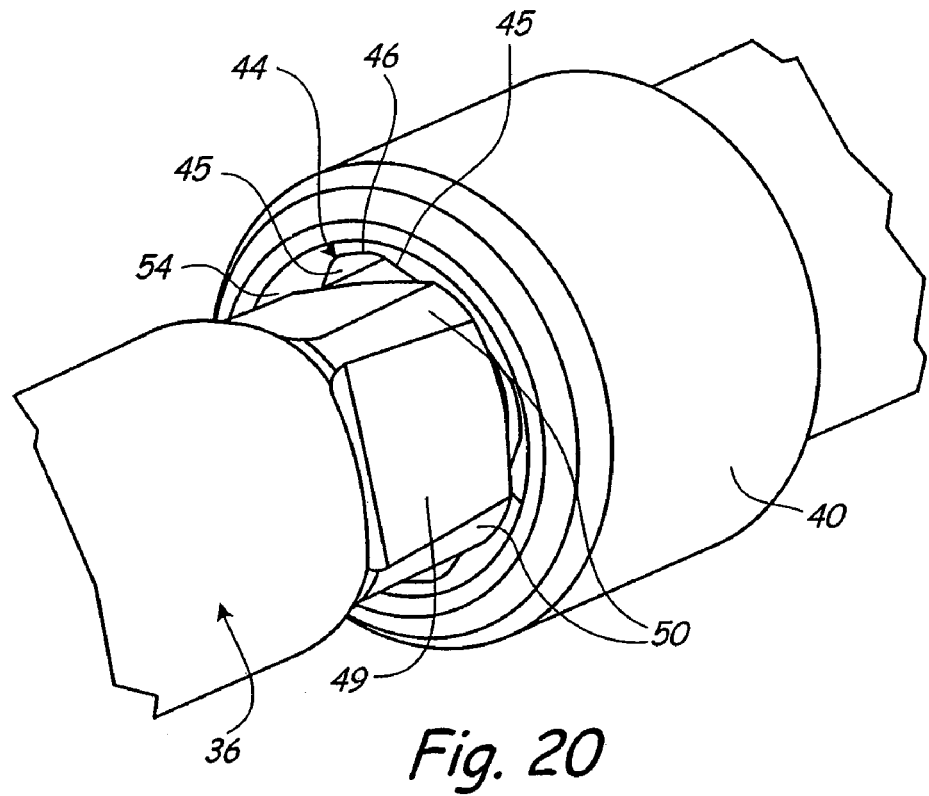
FIG. 20 is an isometric view showing a misaligned driver end being inserted into the abutment screw driving recess.
Figure 21:
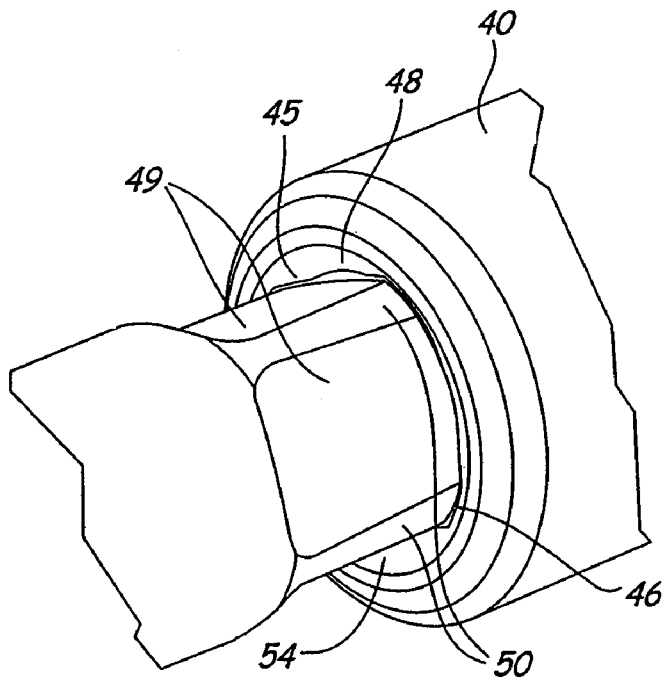
FIG. 21 is a view similar to that of FIG. 20, except with the driver end being aligned.
Figure 23:
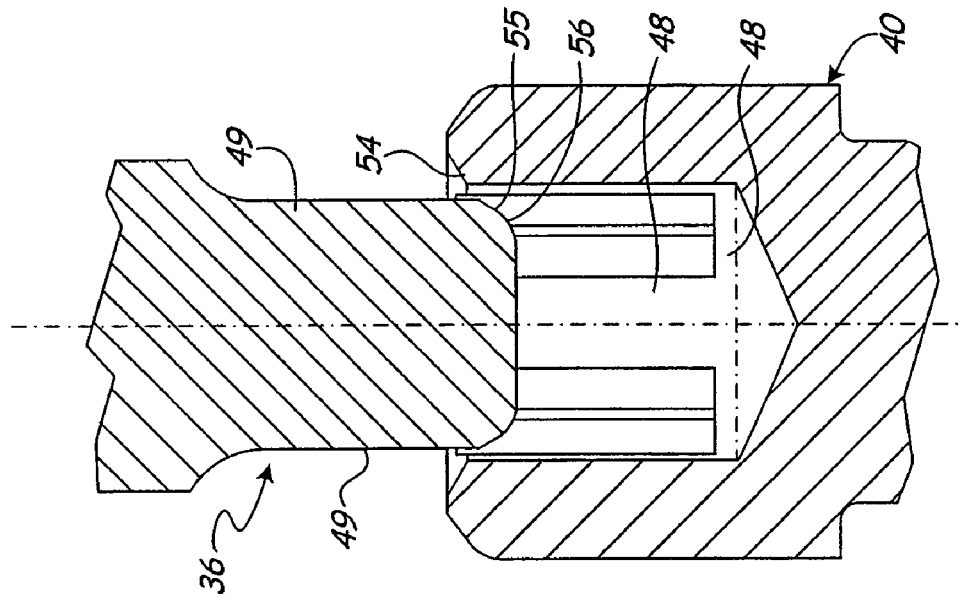
FIG. 23 is a sectional view showing the relationship between the driver end and the driving recess of FIG. 21 when such elements are aligned.
Figure 22:
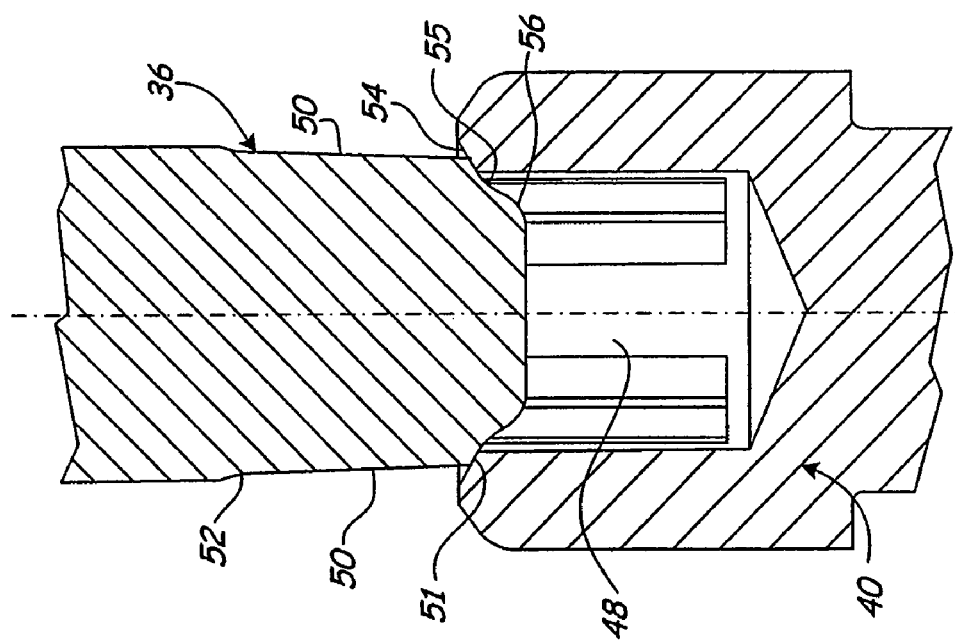
FIG. 22 is a sectional view showing the relationship between the driver end and the driving recess of FIG. 20 when such elements are misaligned.

Reference is next made to FIGS. 20 and 22 showing a misaligned driver end 36 relative to the recess 39 and FIGS. 21 and 23 showing an aligned driver end 36 relative to the recess 39. If the driver end 36 is misaligned as shown in FIGS. 20 and 22, the driver end 36 will be immediately axially aligned as a result of engagement between the surface portions 55 and 56 at the distal end of the end 36 and the pilot bore 48. Then, upon rotation of the driver end 36, engagement between the beveled surface 54 on the screw 40 and the radiused surface portion 55 on the driver end 36, the drive end 36 will drop into the recess 39, with the interference surfaces 50 aligned and engaged with the end portion 46.

Although the description of the preferred embodiment has been quite specific, it is contemplated that various modifications could be made without deviating from the spirit of the present invention. Accordingly, it is intended that the scope of the present invention be dictated by the appended claims rather than by the description of the preferred embodiment.

The invention claimed is:

1. A self-aligning dental component carry and drive assembly, comprising:
   a dental component having a driving recess; and
   a carry and drive device comprising:
      a driver end having a distal end and a proximal end, the driver end including four generally planar drive surfaces each extending from the distal end to the proximal end of the driver end and being adapted to engage at least one surface within the driving recess of the dental component;
      at least one interference surface, wherein each interference surface is positioned between adjacent drive surfaces of the driver end, and each interference surface is beveled to incline inwardly toward a central axis of the driver end as the interference surface extends from the proximal end to the distal end of the driver end to enable frictional carrying engagement between the driver end and the driving recess of the dental component upon insertion of the driver end into the driving recess; and a pilot portion extending from the distal end of the driver end, the pilot portion comprising an aligning surface portion and a radiused surface portion proximally adjacent to the aligning surface portion, wherein the aligning surface portion is configured to align the central axis of the driver end with a central axis of the driving recess of the dental component, and wherein the radiused surface portion is configured to rotate on a beveled surface in the driving recess to enable alignment of the drive surfaces of the driver end with the at least one surface in the driving recess upon rotation of the driver end in the driving recess.

2. The self-aligning carry and drive assembly of claim 1, wherein the driver end has a generally square cross-section extending from the distal end to the proximal end of the driver end.

3. The self-aligning carry and drive assembly of claim 1, wherein the driving recess includes an accommodation region to accommodate the pilot portion upon engagement of the driver end in the driving recess.

4. The self-aligning carry and drive assembly of claim 1, wherein the dental component is an abutment screw.

5. A combination comprising:
a dental component having a driving recess; and
a carry and drive device comprising:
a driver end having a distal end and a proximal end, the driver end including four generally planar drive surfaces each extending from the distal end to the proximal end of the driver end and being adapted to engage at least one surface within the driving recess of the dental component;
at least one interference surface, wherein each interference surface is positioned between adjacent drive surfaces of the driver end, and each interference surface is beveled to incline inwardly toward a central axis of the driver end as the interference surface extends from the proximal end to the distal end of the driver end to enable frictional carrying engagement between the driver end and the driving recess of the dental component upon insertion of the driver end into the driving recess; and
a pilot portion extending from the distal end of the driver end, the pilot portion comprising an aligning surface portion and a radiused surface portion proximally adjacent to the aligning surface portion, wherein the aligning surface portion is configured to align the central axis of the driver end with a central axis of the driving recess of the dental component, and wherein the radiused surface portion is configured to rotate on a beveled surface in the driving recess to enable alignment of the drive surfaces of the driver end with the at least one surface in the driving recess upon rotation of the driver end in the driving recess.

6. The combination of claim 5, wherein the driver end has a generally square cross-section extending from the distal end to the proximal end of the driver end.

7. The combination of claim 5, wherein the driving recess includes an accommodation region to accommodate the pilot portion upon engagement of the driver end in the driving recess.

8. The combination of claim 5, wherein the dental component is an abutment screw.

9. A self-aligning dental component carry and drive assembly, comprising:
a dental component having a driving recess; and
a carry and drive device comprising:
a driver end having a distal end and a proximal end, the driver end including a plurality of drive surfaces each comprising either a concave or a convex driving lobe and extending from the distal end to the proximal end of the driver end and being adapted to engage at least one surface within the driving recess of the dental component;
at least one interference surface, wherein each interference surface is positioned on a surface of a concave or convex driving lobe of one of the drive surfaces of the driver end, and each interference surface is beveled to incline inwardly toward a central axis of the driver end as the interference surface extends from the proximal end to the distal end of the driver end to enable frictional carrying engagement between the driver end and the driving recess of the dental component upon insertion of the driver end into the driving recess; and
a pilot portion extending from the distal end of the driver end, the pilot portion comprising an aligning surface portion and a radiused surface portion proximally adjacent to the aligning surface portion, wherein the aligning surface portion is configured to align the central axis of the driver end with a central axis of the driving recess of the dental component, and wherein the radiused surface portion is configured to rotate on a beveled surface in the driving recess to enable alignment of the drive surfaces of the driver end with the at least one surface in the driving recess upon rotation of the driver end in the driving recess.

10. The self-aligning carry and drive assembly of claim 9, wherein the driving recess includes an accommodation region to accommodate the pilot portion upon engagement of the driver end in the driving recess.

11. The self-aligning carry and drive assembly of claim 9, wherein the dental component is a dental implant.

12. The self-aligning carry and drive assembly of claim 9, wherein the driver end comprises six convex driving lobes.

13. A combination comprising:
a dental component having a driving recess; and
a carry and drive device comprising:
a driver end having a distal end and a proximal end, the driver end including a plurality of drive surfaces each comprising either a concave or a convex driving lobe and extending from the distal end to the proximal end of the driver end and being adapted to engage at least one surface within the driving recess of the dental component;
at least one interference surface, wherein each interference surface is positioned on a surface of a concave or convex driving lobe of one of the drive surfaces of the driver end, and each interference surface is beveled to incline inwardly toward a central axis of the driver end as the interference surface extends from the proximal end to the distal end of the driver end to enable frictional carrying engagement between the driver end and the driving recess of the dental component upon insertion of the driver end into the driving recess; and
a pilot portion extending from the distal end of the driver end, the pilot portion comprising an aligning surface portion and a radiused surface portion proximally adjacent to the aligning surface portion, wherein the aligning surface portion is configured to align the central axis of the driver end with a central axis of the driving recess of the dental component, and wherein the radiused surface portion is configured to rotate on a beveled surface in the driving recess to enable alignment of the drive surfaces of the driver end with the at least one surface in the driving recess upon rotation of the driver end in the driving recess.

14. The combination of claim 13, wherein the driving recess includes an accommodation region to accommodate the pilot portion upon engagement of the driver end in the driving recess.

15. The combination of claim 13, wherein the dental component is a dental implant.

16. The combination of claim 15, wherein the driver end comprises six convex driving lobes.

* * * * *